(12) United States Patent
Wirtz et al.

(10) Patent No.: US 10,918,304 B2
(45) Date of Patent: Feb. 16, 2021

(54) RHEOLOGY SYSTEM AND MR RHEOLOGY SYSTEM WITH RHEOLOGY SENSOR FEEDBACK CONTROL

(71) Applicant: KONINKLIJKE PHILIPS N.V., Eindhoven (NL)

(72) Inventors: Daniel Wirtz, Eindhoven (NL); Christoph Leussler, Eindhoven (NL); Peter Mazurkewitz, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 463 days.

(21) Appl. No.: 15/128,121

(22) PCT Filed: Mar. 26, 2015

(86) PCT No.: PCT/EP2015/056526
§ 371 (c)(1),
(2) Date: Sep. 22, 2016

(87) PCT Pub. No.: WO2015/144811
PCT Pub. Date: Oct. 1, 2015

(65) Prior Publication Data
US 2017/0086703 A1 Mar. 30, 2017

(30) Foreign Application Priority Data
Mar. 26, 2014 (EP) .................... 14161722

(51) Int. Cl.
*A61B 5/055* (2006.01)
*A61B 5/00* (2006.01)
*G01R 33/563* (2006.01)

(52) U.S. Cl.
CPC ............ *A61B 5/055* (2013.01); *A61B 5/0051* (2013.01); *G01R 33/56358* (2013.01)

(58) Field of Classification Search
CPC ..... A61B 5/055; A61B 5/0051; A61B 5/0048; A61B 5/0053; A61B 5/72; A61B 5/721;
(Continued)

(56) References Cited

U.S. PATENT DOCUMENTS

2004/0106880 A1* 6/2004 Weng .................. A61B 8/4422
601/2
2006/0012367 A1* 1/2006 Meaney .................. A61B 5/05
324/315
(Continued)

FOREIGN PATENT DOCUMENTS

EP 1720028 A1 * 11/2006 ....... G01R 33/56358
EP 1720028 A1 11/2006
(Continued)

OTHER PUBLICATIONS

Mariappan et al "Magnetic Resonance Elastography with a Phased-Array Acoustic Driver System" Magnetic Resonance in Med. vol. 61, p. 678-685 (2009).*
(Continued)

*Primary Examiner* — Patricia J Park
*Assistant Examiner* — Victoria Fang

(57) ABSTRACT

A rheology system (202) includes a rheology transducer device (204) for introducing mechanical waves into a subject of interest (120). The rheology transducer device (204) includes multiple transducers (212), a driving device (206) for driving the rheology transducer device (204), a sensor device (208) for sensing mechanical waves at the subject of interest (120), and a control device (210) for receiving input from the sensor device (208) and for controlling the driving device (206) based on the received input from the sensor device (208). An MR rheology system (200) includes the above rheology system (202) and an MR imaging system (110) adapted to control the rheology system (200). A rheology method includes with the rheology system (202), (Continued)

driving the rheology transducer device (204) to introduce mechanical waves into the subject of interest (120), sensing mechanical waves at the subject of interest (120), and performing feedback control.

20 Claims, 8 Drawing Sheets

(58) Field of Classification Search
CPC ......... A61B 5/4836; A61B 8/08; A61B 8/485;
A61B 2018/00636; A61B 2018/00642;
A61B 2018/00648; A61B 2018/00654;
A61B 2018/0066; A61B 2018/00684;
A61B 2018/00696; A61B 2018/00732;
A61B 2018/0075; A61B 2018/00773;
A61B 2018/00845; A61B 2018/00869;
A61B 2018/0088; A61B 2018/00988;
A61B 2090/374; G01R 33/30; G01R 33/56358
USPC ........ 600/411, 410, 419, 421, 437, 438, 459
See application file for complete search history.

(56) References Cited

U.S. PATENT DOCUMENTS

| | | | | |
|---|---|---|---|---|
| 2009/0209847 A1* | 8/2009 | Li | ................. | A61B 5/055 600/421 |
| 2009/0221917 A1* | 9/2009 | Southern | .............. | A61B 5/0048 600/444 |
| 2012/0053450 A1* | 3/2012 | Salcudean | ............ | A61B 5/0051 600/421 |
| 2013/0116561 A1* | 5/2013 | Rothberg | ............. | A61B 8/4254 600/438 |
| 2013/0289593 A1* | 10/2013 | Hall | ............... | A61B 17/320068 606/169 |
| 2013/0303882 A1* | 11/2013 | Kolipaka | ............... | A61B 5/055 600/415 |
| 2019/0192119 A1* | 6/2019 | Salcudean | ........... | G01S 7/52042 |

FOREIGN PATENT DOCUMENTS

| | | | |
|---|---|---|---|
| WO | WO-1999023940 A1 * | 5/1999 | |
| WO | 2014040954 A1 | 3/2014 | |
| WO | WO-2014040954 A1 * | 3/2014 | ....... G01R 33/56358 |

OTHER PUBLICATIONS

Sinkus R, Lorenzen J, Schrader D, Lorenzen M, Dargatz M, Holz D.High-resolution tensor MR elastography for breast tumour detection. Phys Med Biol 2000;45:1649-1664.

Sinkus R. et al "MR Elastography of Breast Legions Understanding the Solid.." Magnetic Resonance in Medicine 58:1135-1144 (2007).

Rossman P. et al Piezoelectric Bending Elements for use as Motion Actuators in MR Elastography: Proc. Intl. Soc. Mag. Reson. Med. 11 (2003) p. 1075.

* cited by examiner

RHEOLOGY SYSTEM AND MR RHEOLOGY SYSTEM WITH RHEOLOGY SENSOR FEEDBACK CONTROL

CROSS REFERENCE TO RELATED APPLICATIONS

This application is a U.S. national phase application of International Application No. PCT/EP2015/056526, filed on Mar. 26, 2015, which claims the benefit of EP Application Serial No. 14161722.5 filed on Mar. 26, 2014 and is incorporated herein by reference.

FIELD OF THE INVENTION

The invention relates to the field of magnetic resonance (MR) rheology imaging.

BACKGROUND OF THE INVENTION

In the area of magnetic resonance (MR) imaging, MR rheology is a technique for gathering additional information on tissue properties, which is not accessible with MR imaging alone. For this purpose, low-frequency mechanical waves are coupled into tissue of a subject of interest, which is driven to oscillate. This oscillation leads to certain effects including shear waves causing MR imaging contrast, if using MR sequences phase-locked to the mechanical excitation. MR rheology is capable of providing information, which was formerly available, e.g. via palpation. Hence, palpation has turned into the assessment of an objective absolute physical quantity, whose diagnostic value can be quantified. This information can be used to distinguish tissue, e.g. healthy or malign tissue, based on its viscoelastic properties and leads to a substantial rise in specificity in MR imaging. Detailed parameters like tissue viscosity or elasticity can otherwise only be determined using biopsy and/or histology. It has been demonstrated that these tissue properties can help in the detection of cirrhotic or cancerous changes, e.g. in liver, breast or brain tissue. In particular, MR rheology has been proven to be especially useful for determining and staging liver cirrhosis as well as breast cancer. Initial applications to degenerative brain diseases have also been proposed. MR Rheology has emerged as a powerful tool providing additional diagnostic information to the radiologist compared to MR imaging alone.

The MR rheology is based on mechanical waves introduced into the subject of interest, typically a human patient. Nevertheless, MR imaging in general and MR rheology in particular are also applicable to any kind of animal or even for the purpose of analyzing materials. The oscillation of the tissue is achieved by attaching at least one mechanical transducer to the subject of interest close to a region of interest, for which an image is desired. A number of different transducers for employing the mechanical oscillation to the tissue of the subject of interest have been proposed and demonstrated, e.g. electromagnetic designs, which make use of the BO-field inside a MR imaging device, piezo-driven transducers or pneumatic transducers. E.g. a sinusoidal acoustic wave can be coupled to the subject of interest using a transducer resulting in a mechanical wave propagating through the subject of interest. The transducer is connected to a driving unit that allows active control of individual amplitude, phases and vibration frequency. When performing MR imaging triggered on the vibrational excitation frequency, viscoelastic tissue parameters can be deduced from the phase variation between subsequent MR images.

Commonly used rheology transducers are single channel devices. That allows for a use at various anatomical positions but significantly narrows its possible application with regard to excitation quality and diagnostic value. Moreover exact placement of such a transducer is critical since the area of contact between a piston of the transducer, which introduces the mechanical wave into the subject of interest by a one-dimensional axial movement, and the subject of interest is fixed by initial placement. The resulting mechanical wave has to be taken 'as is'. The only parameters, that can be modified, are vibrational amplitude, phase and frequency. An optimization of the excitation parameters is not easily achievable and usually depends on trial and error. Furthermore, the adaption of mechanical matching to the patient's body is solely provided by initial placement of the single channel device.

It is also known in the Art to employ a transducer device with a transducer array driven by multiple drivers. The strain waves produced by each driver in an array can be separately controlled in amplitude and phase to produce a desired pattern of strain in the region of interest of the subject of interest when played together. Hence, the phase and amplitude of their strain waves of the different transducers can be controlled to commonly provide a desired pattern of strain in the region of interest of the subject of interest. The suspect tumor tissues can thus be caused to oscillate during the MR imaging to provide information from which its stiffness and other mechanical characteristics may be determined. Accordingly, a differentiation between e.g. tumors and surrounding tissue can be performed based on the MR rheology images, so that the tumor can be delineated. Once a tumor is delineated, it can be of interest to study only the tumor to gain further insight into the tumor's properties using the desired pattern of strain in the region of interest of the subject of interest.

When performing MR rheology methods, the behavior of the mechanical waves within the tissue like propagation, reflection and scattering is very important. Nevertheless, the behavior depends on the properties of the medium through which the mechanical wave passes, i.e. the tissue properties. It is possible to determine the medium's properties, if the wave pattern is known prior to generating the MR rheology imaging, thereby e.g. increasing the time required for generation of the MR rheology images, since the wave pattern can be measured e.g. using MR imaging. This reduces the efficiency in using MR imaging devices, since additional MR images have to be provided.

In this context, according to document EP 1 720 028 A1, a magnetic resonance elastography (MRE) scan is performed using an array of transducers for applying a strain wave to tissues in a region of interest. A calibration process is performed prior to the scan in which the strain wave produced by each transducer in the array is imaged using an MRE pulse sequence so that information may be acquired that enables each transducer to be properly driven during a subsequent MRE scan.

Furthermore, document WO 2014/040954 A1 refers to a medical instrument comprising a magnetic resonance imaging system, a transducer for mechanically vibrating at least a portion of the subject within the imaging zone. Instructions cause a processor controlling the medical instrument to control the transducer to vibrate; control the magnetic resonance imaging system to repeatedly acquire the magnetic resonance data using a first spatially encoding pulse sequence; control the magnetic resonance imaging system to acquire navigator data using a second spatially encoding pulse sequence; construct a set of navigator profiles using the navigator data; determine at least one parameter descriptive of transducer vibrations using the set of navigator profiles; and reconstruct at least one magnetic resonance rheology image from the magnetic resonance data.

SUMMARY OF THE INVENTION

It is an object of the invention to provide a rheology system and a magnetic resonance (MR) rheology system comprising a rheology system for improved MR imaging with rheology information in an efficient way. In particular, it is an object of the present invention to provide the rheology system and the MR rheology system for a reliable introduction of mechanical waves into a desired region of interest of a subject of interest in an efficient way. Furthermore, it is an object of the invention to provide methods for providing improved MR images containing rheology information, in particular for providing MR images containing rheology information of a desired region of interest of a subject of interest, in an efficient way.

This object is achieved by a rheology system comprising a rheology transducer device for introducing mechanical waves into a subject of interest, whereby the rheology transducer device comprises multiple transducers, a driving device for driving the rheology transducer device, a sensor device for sensing mechanical waves at the subject of interest, and a control device for receiving input from the sensor device and for controlling the driving device based on the received input from the sensor device, whereby the rheology transducer device is provided as nail board transducer device comprising a fixture, the multiple transducers are provided as nail-like transducers, and the multiple nail-like transducers are commonly arranged and attached to the fixture to be commonly located at the subject of interest.

This object is also achieved by a MR rheology system comprising a MR imaging system, and a rheology system as specified above, whereby the MR imaging system is adapted to control the rheology system.

A feature of the rheology system is sensing the rheology excitation introduced into the subject of interest. This enables determining the mechanical wave inside the subject of interest, e.g. propagation direction, amplitude and phase distribution of the region of interest. This information can be used to manipulate the mechanical wave when being introduced into the subject of interest. This enables a kind of steering of the mechanical wave into the region of interest using interference individual mechanical excitations, similar to e.g. 'beam steering' as known from HIFU devices or others. Accordingly, improved signal to noise ratio and excitation of deep lying tissue within the subject of interest can be achieved.

In more detail, the rheology transducer device and the sensor device are located at the subject of interest to introduce mechanical waves into a region of interest of the subject of interest and to sense the mechanical waves at a surface of the subject of interest. The sensor device is preferably located at an opposite side of the subject of interest compared to the rheology transducer device. Hence, the sensor device can sense the mechanical waves, which have traversed the subject of interest starting from the rheology transducer device. The input from the sensor device can be used to determine the propagation of the mechanical wave within the subject of interest, so that the mechanical waves in the region of interest can be determined with a high reliability. Improvements can be provided by a combination of the sensor input from the sensor device with anatomical models, allowing for a more detailed evaluation of the mechanical wave inside the subject of interest. Feedback control can be performed by adaptation of the mechanical waves introduced into the subject of interest in respect to frequency, amplitude, and phase. These parameters can be determined for each transducer of the rheology transducer device, or commonly for groups of transducers. The introduction of a desired mechanical wave into a region of interest of the subject of interest enables MR imaging to obtain MR images of the region of interest with rheology information with high accuracy and efficiency. For example, rheology information e.g. of organs, i.e. soft tissue, which are located close to the spinal column, i.e. hard tissue, can be reliably generated.

The sensor device can comprise any kind of suitable sensor, e.g. an acoustic sensor, a microphone, a vibration sensor, or an accelerometer, which can be positioned in contact with the subject of interest.

Typically, the rheology transducer device can be used to replace one transducer as known in the Art, e.g. a single channel transducer. This is without prejudice to the ability of using more than one rheology transducer device and forming an array of rheology transducer devices, while each of the rheology transducer devices can perform an arbitrary wave pattern. Preferably, the rheology transducer device has a pre-shaped form that ensures optimized coupling of the mechanical wave into the subject of interest. Further preferred, different rheology transducer devices can be provided optimized in size and form e.g. for rheology of the head, the prostate, the sternum or other parts of the subject of interest. Multiple transducers allow the application of several spatially separated excitations of mechanical waves, each of which adjustable in amplitude and frequency as well as excitation phase relative to the other transducers. Furthermore, the phase of the mechanical waves can be adjusted relative to an acquisition signal indicating the beginning of an MR imaging sequence. The multiple transducers enable applications like "beam steering" of the mechanical wave and excitation of deep lying tissue. Moreover shimming of the desired density fluctuation inside the subject of interest can be realized.

Preferably, the MR rheology device is adapted to provide additional information suitable for determining the mechanical wave inside the subject of interest, in particular inside the region of interest. E.g. the MR rheology can be adapted to provide and process additional MR imaging information to determine the mechanical wave inside the subject of interest. Another means for determining the mechanical wave introduced into the subject of interest for an electrically driven rheology transducer device is monitoring the current through each transducer.

According to a preferred embodiment the sensor device for sensing mechanical waves at the subject of interest comprises multiple sensors for sensing mechanical waves at the subject of interest, whereby the multiple sensors are arranged to sense the mechanical waves at different locations of the subject of interest. The sensor can be acoustic sensors, microphones, vibration sensor, and accelerometers. Furthermore, the sensor device may also comprise combinations of different kinds of sensors. The sensors may be attached to each other in any suitable way to facilitate handling thereof. E.g., when the sensors are connected to each other, they can be connected to the control device by means of a single cable, which transmits sensor signals from the multiple sensors. The connection is preferably flexible to enable a reliable placement in contact with the subject of interest. Individual sensors, which are not attached to each other, can be used to cover the subject of interest at locations, which are no not close by, e.g. on different sides thereof, so that the placement of individual sensors is not restricted by the placement of other sensors. Multichannel sensing of the mechanical wave generated by the rheology transducer device allows for acoustic shimming of amplitude and phase of the introduced mechanical wave. Multiple sensors can be implemented as independent reception channels, thereby enabling a detailed evaluation of the mechanical wave inside the subject of interest, in particular inside the region of interest. Accordingly, the excitation of deep lying tissue, i.e. tissue deep below a surface of the subject of interest, as well as directing a mechanical wave into a desired region of interest, can be realized.

According to a preferred embodiment the multiple sensors for sensing mechanical waves at the subject of interest are commonly arranged with predefined distances between each other. Preferably, the multiple sensors are commonly arranged with equal distances between each other in at least one direction. Further preferred, the multiple sensors are commonly arranged in a net-like structure. The structure is preferably flexible to allow adaptation to different shapes depending on the area of the subject of interest where the multiple sensors are located. The known distances facilitate the processing of the received input from the multiple sensors to determine the mechanical wave within the underlying tissue. Accordingly, the rheology transducer device can be easily driven using the input from the multiple sensors.

According to a preferred embodiment the rheology transducer device comprises a fixture, and the multiple transducers are attached to the fixture to be commonly located at the subject of interest. The fixture can be any kind of suitable fixture for fixing the transducers together, so that they can be positioned together and in a simple way at the subject of interest. Preferably, the multiple transducers are attached to the fixture with predefined distances between each other. Preferably, the multiple transducers are fixed with equal distances between each other to the fixture in at least one direction. Further preferred, the multiple transducers are commonly arranged in a net-like structure. The known distances facilitate the control of the multiple transducers to generate the desired mechanical wave within the subject of interest at the desired region of interest. Preferably, the fixture is adapted to a typical size and/or shape of the subject of interest, e.g. under consideration of a region of interest. Hence, different fixtures can be used depending on the desired placement of the rheology transducer device. Further preferred, the fixture is adaptable to different shapes of the subject of interest. The fixture can for example be flexible. The better the multiple transducers are in contact with the subject of interest, the better the mechanical waves can be introduced into the subject of interest, thereby enhancing the possible quality of MR imaging.

According to a preferred embodiment the rheology transducer device is provided as nail board transducer device, whereby multiple nail-like transducers are commonly arranged. The transducers can e.g. be arranged in a planar manner by the fixture. Furthermore, the transducers can be provided in a planar array. With the nail board transducer device, multiple transducers can be arranged close together, which facilitates the introduction of mechanical waves into the subject of interest. The individual transducers can be easily driven to introduce desired mechanical waves into the subject of interest to generate a mechanical wave within a region of interest. According to a preferred embodiment the transducers are covered with a diaphragm due to comfort of the subject of interest and performance reason. The diaphragm covers at least the part of the nail board transducer to be placed in contact with the subject of interest. Preferably, the transducers are adjustable in their longitudinal direction, i.e. the direction of the movement of the transducers, so that they can be in contact with the subject of interest, e.g. when the surface of the subject of interest is not planar. Further preferred, the nail board transducer device can be switched between an adjustment mode, where the transducers are movable along their longitudinal direction, and an operation mode, where the transducers are not movable along their longitudinal direction relative to the fixture. Still further preferred, the transducers are provided as auto-adapting transducers, which automatically adapt to the shape of the subject of interest.

According to a preferred embodiment the rheology transducer device comprises at least one drive unit for driving multiple transducers to introduce a mechanical wave into a region of interest of the subject of interest upon reception of a single driving signal from the driving device. Hence, one drive signal from the driving device can be used to drive multiple transducers. The number of drive signals provided from the driving device can vary. E.g. a single drive signal may be provided from the driving device to drive the transducers of the entire rheology transducer device, resulting in a single channel rheology transducer device. Alternatively, groups of transducers can be driven by means of a single drive signal from the driving device, whereby each of the drive signals can be used as input for multiple drive units to drive multiple transducers. In all cases, the rheology transducer device can drive the multiple transducers to generate any desired mechanical wave within the subject of interest. Preferably, the rheology transducer device is configurable so that depending on the received drive signal from the driving device the desired mechanical wave can be generated. Accordingly, the control of the transducers can be facilitated in the control device and/or the driving device, since the control device only provides few drive signals for driving the multiple transducers. The remaining control for driving the multiple transducers can be realized in the rheology transducer device, so that processing of signals in the control device and/or in the driving device can be reduced.

According to a preferred embodiment the drive unit is adapted to drive the multiple transducers to introduce the mechanical wave into the region of interest of the subject of interest according to a pre-defined pattern upon reception of the single drive signal. Hence, the rheology transducer device can be configured prior to usage to drive the transducers using the transducer unit(s) in a desired way. The pre-defined patterns can be easily provided to introduce a desired mechanical wave into the subject of interest, so that the control device and/or the driving device can perform a simple and efficient signal processing to introduce a desired mechanical wave into the subject of interest. Preferably, the rheology transducer device comprises a control unit for controlling the driving of the drive units. Hence, the drive unit can apply different modes into the subject of interest based on a single drive signal received from the driving device.

According to a preferred embodiment the multiple transducers are each individually connectable to a drive signal from the driving device. Hence, the rheology transducer device does not comprise means for influencing drive signals from the driving device, and all transducers are directly driven from the driving device. Nevertheless, groups of transducers may be connected to the same drive signal from the driving device. For example, close-by transducers can be driven simultaneously to provide a combined mechanical pulse in an area of the subject of interest.

According to a preferred embodiment the rheology system comprises a look-up table containing drive information based on typical anatomies and sizes of a subject of interest for driving the multiple transducers. Preferably, the look-up table is provided in the control device, the driving device or the rheology transducer device, in particular in the control unit of the rheology transducer device. The rheology system can be adjusted using the lookup-tables, e.g. for typical anatomies and sizes of a subject of interest. The information can be used to control the driving of the transducers, so that desired excitation of a region of interest can easily be achieved. The information from the look-up table is preferably combined with input from the sensor device indicating the actual mechanical wave field produced by the transducers. Also other information suitable for determining the mechanical wave inside the subject of interest can be combined with the information from the Look-up table, MR imaging information and in the case of an electrically driven rheology transducer device the current through each transducer.

The above described rheology system can be used according to the invention in different ways. Accordingly, different methods for rheology can be applied in conjunction with MR imaging to provide improved MR images containing rheology information.

Hence, the object is also achieved by a rheology method comprising the steps of providing a rheology system as specified above with its rheology transducer device and its sensor device in contact to a subject of interest, driving the rheology transducer device to introduce mechanical waves into the subject of interest, sensing mechanical waves at the subject of interest using the sensor device, and performing feedback control for driving the rheology transducer device based on the mechanical waves sensed using the sensor device.

The rheology transducer device and the sensor device are located at the subject of interest to introduce mechanical waves into a region of interest of the subject of interest and to sense the mechanical waves at a surface of the subject of interest. The sensor device is preferably located at an opposite side of the subject of interest compared to the rheology transducer device. Hence, the sensor device can sense the mechanical waves, which have traversed the subject of interest starting from the rheology transducer device. The input from the sensor device can be used to determine the propagation of the mechanical wave within the subject of interest, so that the mechanical waves in the region of interest can be determined with a high reliability. Feedback control can be performed by adaptation of the mechanical waves introduced into the subject of interest in respect to frequency, amplitude, and phase. These parameters can be determined for each transducer of the rheology transducer device, or commonly for groups of transducers. The introduction of a desired mechanical wave into a region of interest of the subject of interest enables MR imaging to obtain MR images of the region of interest with rheology information with high accuracy and efficiency. The multiple transducers enable applications like "beam steering" of the mechanical wave and excitation of deep lying tissue by mechanical waves. Moreover shimming of the desired density fluctuation inside the subject of interest can be realized. Accordingly, improved signal to noise ratio and excitation of deep lying tissue within the subject of interest can be achieved.

With the above method, the rheology system can be used as stand-alone system to be set-up for generating desired mechanical waves in a desired region of interest in the subject of interest during MR imaging. Accordingly, the mechanical waves in the region of interest can be monitored and the control device, the driving device and/or the rheology transducer device can be setup according to the mechanical wave desired in the region of interest. Accordingly, setup times of the MR imaging system for providing rheology images can be reduced, since the rheology setup can be made independently. Preferably, the rheology system can be first located at the subject of interest, i.e. the sensor device and the rheology transducer device can be located at the subject of interest, and the subject of interest can then be transferred into an examination space of the MR imaging system for providing MR rheology images. In this case, the rheology system can first be used individually and then be connected to an MR imaging system to provide MR rheology functionality, thereby forming an MR rheology system.

According to a preferred embodiment the rheology method comprises the additional step of storing control parameters according to the feedback control for driving a rheology transducer device to introduce mechanical waves into the subject of interest without feedback control. The control parameters can be transferred to a MR imaging system, which can then be used to provide MR rheology images based on the stored control parameters. Preferably, the subject of interest keeps connected to the rheology transducer device, so that the positioning of the transducers is maintained, and the subject of interest is moved together with the rheology transducer device into the examination space of the MR imaging system. The MR imaging system can comprise its own control device and or driving device for operating the rheology transducer device. In particular, the control device may be integrally provided with a control device of the MR imaging system. Nevertheless, the driving device may also be transferred together with the rheology transducer device to perform the MR rheology method.

Hence, the object is further achieved by a MR rheology method comprising the steps of performing the rheology method as specified above, introducing mechanical waves into a region of interest of a subject of interest based on the stored control parameters obtained from performing the rheology method, and performing MR image generation containing rheology information of the region of interest of the subject of interest. The MR rheology method provides MR rheology images of the region of interest. Based on the stored control parameters, the mechanical wave can be excited in the region of interest as desired to provide reliable MR rheology images in an efficient way. It is not required to perform the feedback control of the rheology transducer device during the generation of the MR rheology images.

Still further, this object is achieved by a MR rheology method comprising the steps of providing a rheology system as specified above with its rheology transducer device and its sensor device in contact to a subject of interest, driving the rheology transducer device to introduce mechanical waves into the subject of interest, sensing mechanical waves at the subject of interest using the sensor device, performing feedback control for driving the rheology transducer device based on the mechanical waves sensed using the sensor device, and performing MR image generation containing rheology information of the region of interest of the subject of interest. Hence, the rheology system and the MR imaging device are used together to perform continuous feedback control of the rheology transducer device. The continuous feedback control can be performed in addition to a prior determination of the control parameters with the rheology system. Nevertheless, the continuous feedback control can be applied when the MR rheology image generation is started without a prior setup of the rheology system. The continuous feedback control refers to real-time adaptation of the mechanical wave inside the subject of interest. Accordingly, the excitation of the mechanical wave can be adapted e.g. to movements of the subject of interest including breathing.

The object of the present invention is also achieved by a software package for upgrading a magnetic resonance (MR) imaging system, whereby the software package contains instructions for controlling the MR imaging system and the above rheology system 8 according to the above MR rheology method.

The object of the present invention is also achieved by a software package for upgrading a magnetic resonance (MR) imaging system, whereby the software package contains instructions for controlling the MR imaging system and a rheology transducer device for introducing mechanical waves into a subject of interest, whereby the rheology transducer device comprises multiple transducers, according to the above MR rheology method.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
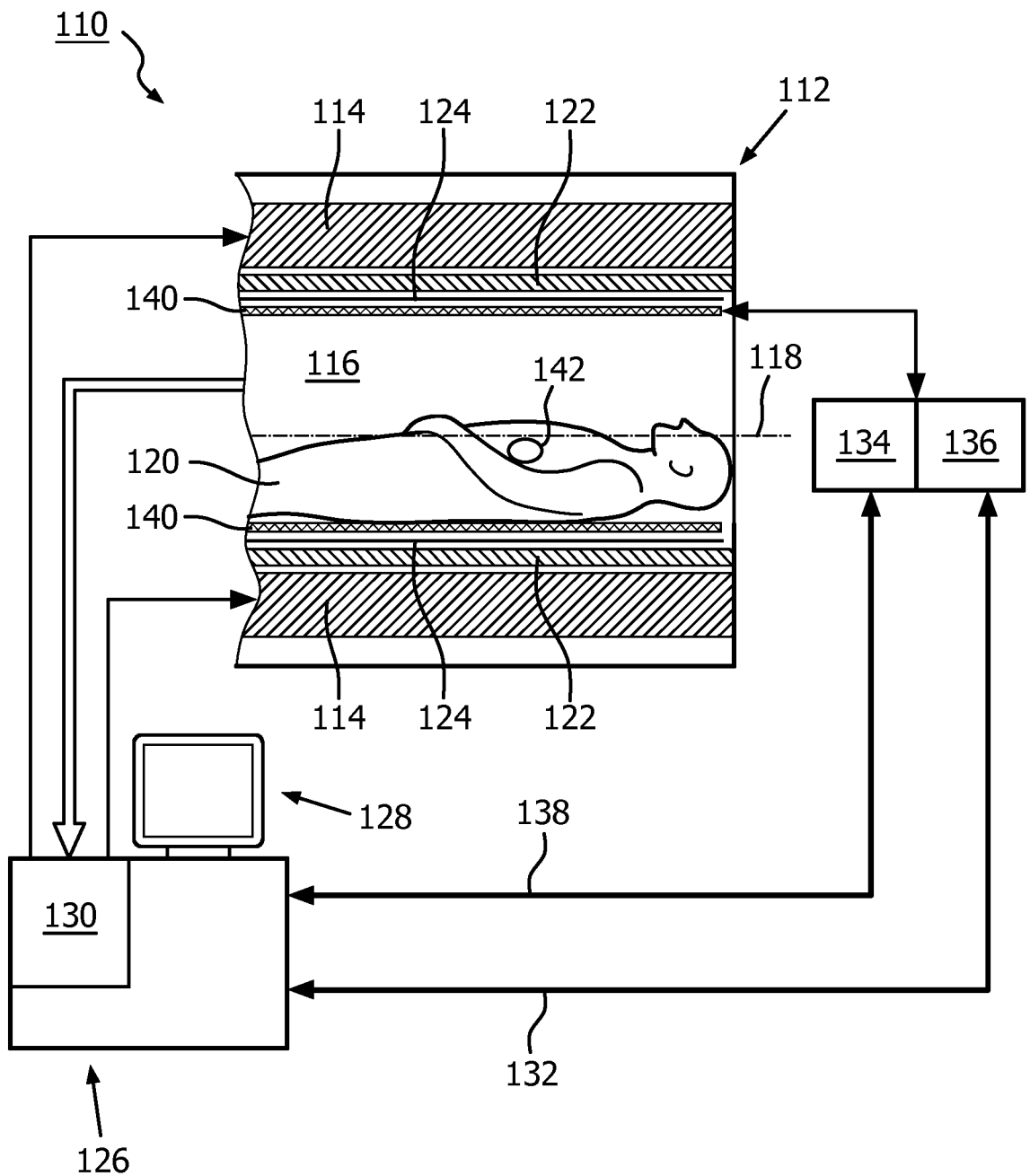
FIG. 1 is a schematic illustration of a part of an embodiment of a magnetic resonance (MR) imaging system in accordance with the invention.

FIG. 1 shows a schematic illustration of a part of an embodiment of a magnetic resonance (MR) imaging system 110 comprising an MR scanner 112. The MR imaging system 110 includes a main magnet 114 provided for generating a static magnetic field. The main magnet 114 has a central bore that provides an examination space 116 around a center axis 118 for a subject of interest 120, usually a patient, to be positioned within. In this embodiment, the central bore and therefore the static magnetic field of the main magnet 114 has a horizontal orientation in accordance with the center axis 118. In an alternative embodiment, the orientation of the main magnet 114 can be different, e.g. to provide the static magnetic field with a vertical orientation. Further, the MR imaging system 110 comprises a magnetic gradient coil system 122 provided for generating gradient magnetic fields superimposed to the static magnetic field. The magnetic gradient coil system 122 is concentrically arranged within the bore of the main magnet 114, as known in the art.

Further, the MR imaging system 110 includes a radio frequency (RF) antenna device 140 designed as a whole-body coil having a tubular body. The RF antenna device 140 is provided for applying an RF magnetic field to the examination space 116 during RF transmit phases to excite nuclei of the subject of interest 120, in particular in a region of interest 142, which shall be covered by MR images. The RF antenna device 140 is also provided to receive MR signals from the excited nuclei during RF receive phases. In a state of operation of the MR imaging system 110, RF transmit phases and RF receive phases are taking place in a consecutive manner. The RF antenna device 140 is arranged concentrically within the bore of the main magnet 114. As is known in the art, a cylindrical metal RF screen 124 is arranged concentrically between the magnetic gradient coil system 122 and the RF antenna device 140.

Moreover, the MR imaging system 110 comprises an MR image reconstruction unit 130 provided for reconstructing MR images from the acquired MR signals and an MR imaging system control unit 126 with a monitor unit 128 provided to control functions of the MR scanner 112, as is commonly known in the art. Control lines 132 are installed between the MR imaging system control unit 126 and an RF transmitter unit 134 that is provided to feed RF power of an MR radio frequency to the RF antenna device 140 via an RF switching unit 136 during the RF transmit phases. The RF switching unit 136 in turn is also controlled by the MR imaging system control unit 126, and another control line 138 is installed between the MR imaging system control unit 126 and the RF switching unit 136 to serve that purpose. During RF receive phase, the RF switching unit 136 directs the MR signals from the RF antenna device 140 to the MR image reconstruction unit 130 after pre-amplification.

Figure 2:
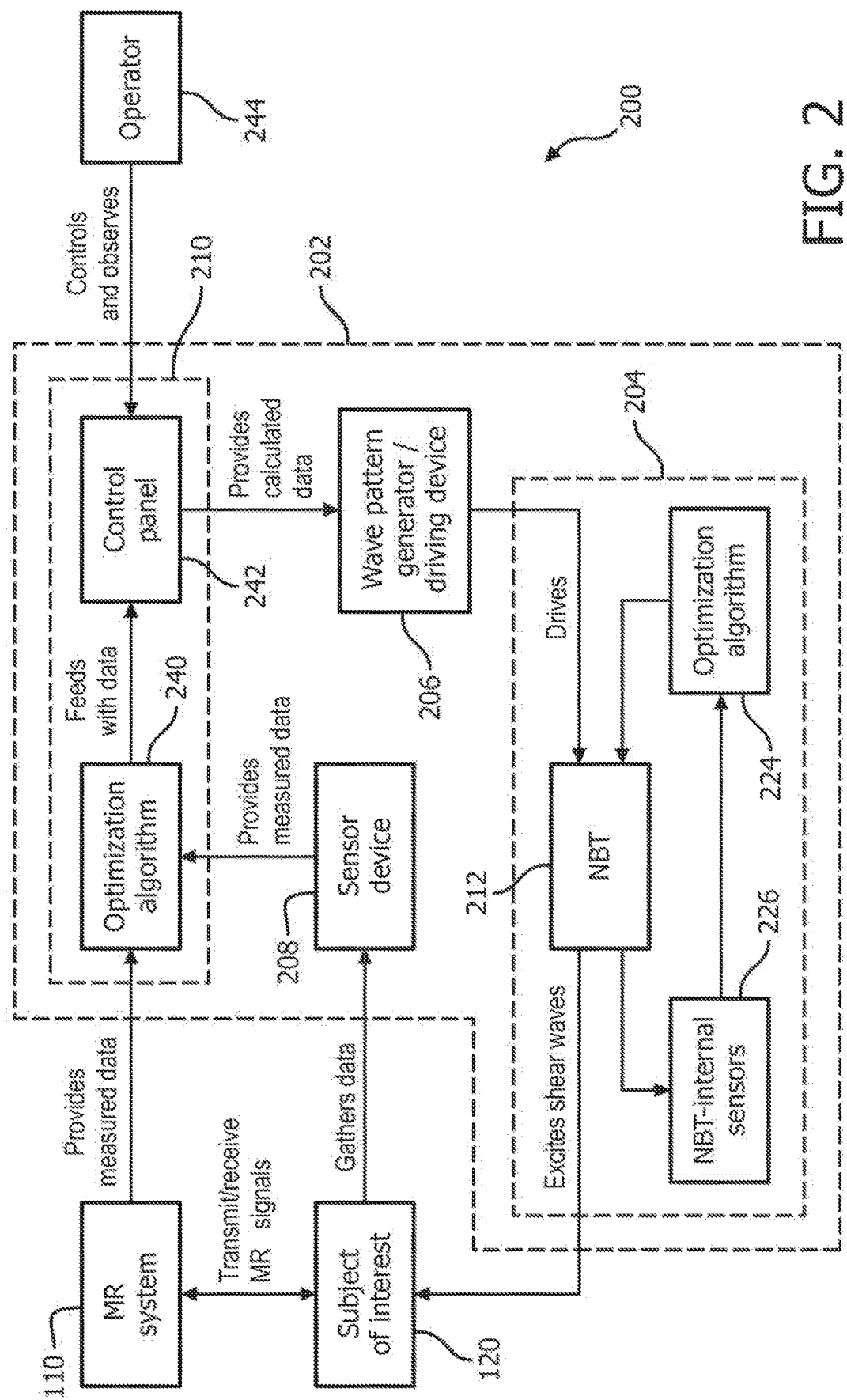
FIG. 2 is a diagram showing a functional system description of a MR rheology system with a subject of interest.
Figure 3:
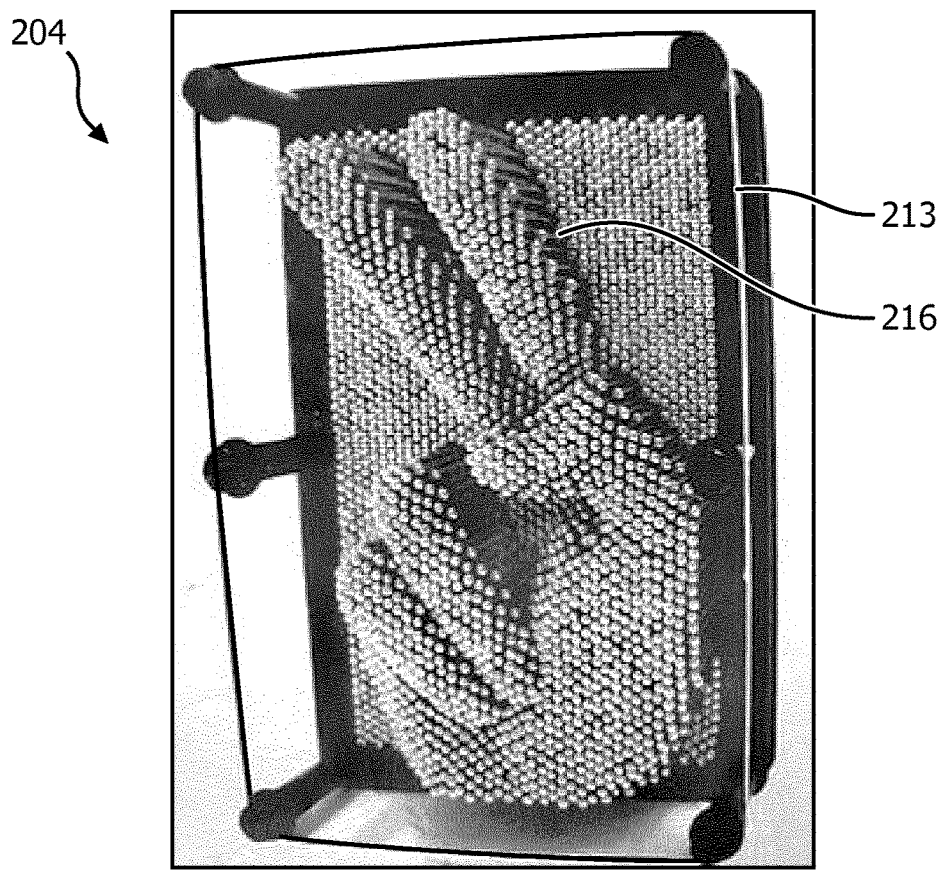
FIG. 3 is a schematic drawing of a rheology transducer device provided as a nail board transducer of the rheology system of FIG. 2 according to a first embodiment.
Figure 4:
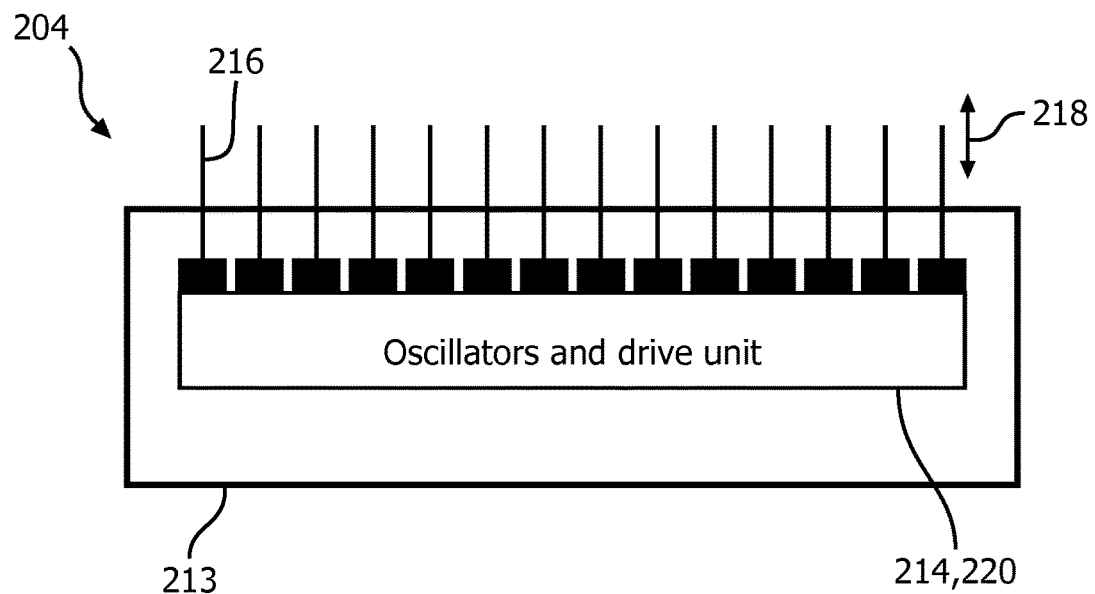
FIG. 4 is a schematic drawing of the rheology transducer device of the rheology system shown in FIG. 3.

FIGS. 2 to 4 refer a MR rheology system 200 according to a first embodiment. The MR rheology system 200 comprises in addition to the above MR imaging system 110 a rheology system 202, as can be seen schematically in FIG. 2.

As can be seen in detail in FIG. 2, the rheology system 202 according to the first embodiment comprises a rheology transducer device 204 for introducing mechanical waves into the subject of interest 120, a driving device 206 for driving the rheology transducer device 204, a sensor device 208 for sensing mechanical waves at the subject of interest 120, and a control device 210 for receiving input from the sensor device 208 and for controlling the driving device 206 based on the received input from the sensor device 208. Although not shown in FIG. 2, the MR imaging system 110 is adapted to control the rheology system 202 via a respective control line, which is not shown in the figures.

A rheology transducer device 204 according to the first embodiment can be seen with respect to FIGS. 3 and 4 with more detail. The rheology transducer device 204 of the first embodiment is provided as nail board transducer device, whereby multiple transducers 212 are commonly arranged and attached to a fixture 213. The transducers 212 are provided as nail-like transducers 212 and are arranged with predefined, equal distances between each other in the form of a planar array. The fixture 213 is adapted to a typical size of the subject of interest 120 under consideration of the region of interest 142. Each transducer 212 comprises a piston 216, which is movable in the direction of its longitudinal axis, as indicated by arrow 218, by an oscillator 220. Accordingly, the each transducer in contact with the subject of interest 120 can introduce a mechanical wave into the subject of interest 120 by movement of its piston 216.

The part of the rheology transducer device 204 to be placed in contact with the subject of interest 120 is covered with a diaphragm, which is not shown in the figures, due to comfort of the subject of interest 120 and performance reason. The transducers 212 of the first embodiment are adjustable in their longitudinal direction, i.e. the direction of the movement of the piston of the transducers 212. In particular, the transducers 212 are provided as auto-adapting transducers 212, which automatically adapt to the shape of the subject of interest 120.

As can be seen in FIGS. 2 and 4, the rheology transducer device 204 of the first embodiment comprises one drive unit 214 for driving the transducers 212. The rheology transducer device 204 comprises a control unit 224 for controlling the drive unit 214 based on a received drive signal from the driving device 206. Hence, the transducers 212 of the rheology transducer device 204 of the first embodiment are driven upon reception of a single driving signal from the driving device 206, i.e. one drive signal from the driving device 206 drives all transducers 212. Accordingly, the rheology transducer device 204 is provided as single channel rheology transducer device 204. Hence, as indicated in FIG. 2, the control unit 224 controls the driving of all transducers 212 of the rheology transducer device 204.

As can be further seen in FIG. 2, the rheology transducer device 204 comprises internal sensors 226, which are current sensors in this embodiment. The internal sensors 226 provide feedback information on the excitation of the mechanical wave with the rheology transducer device 204. The feedback is passed to the control unit 224, which processes the feedback information for driving the transducers 212.

Figure 5:
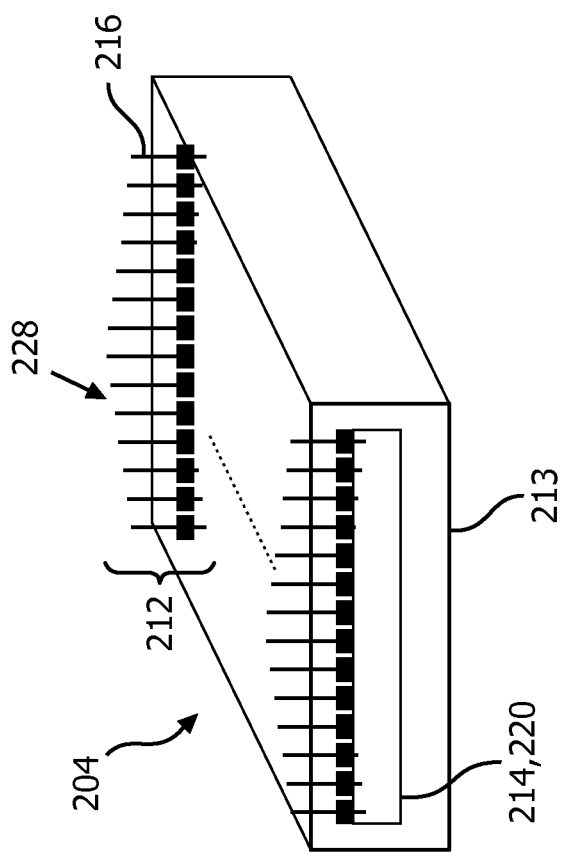
FIG. 5 is a schematic drawing of a mechanical wave generated using the nail board transducer according to the first embodiment in a perspective view.
Figure 5:
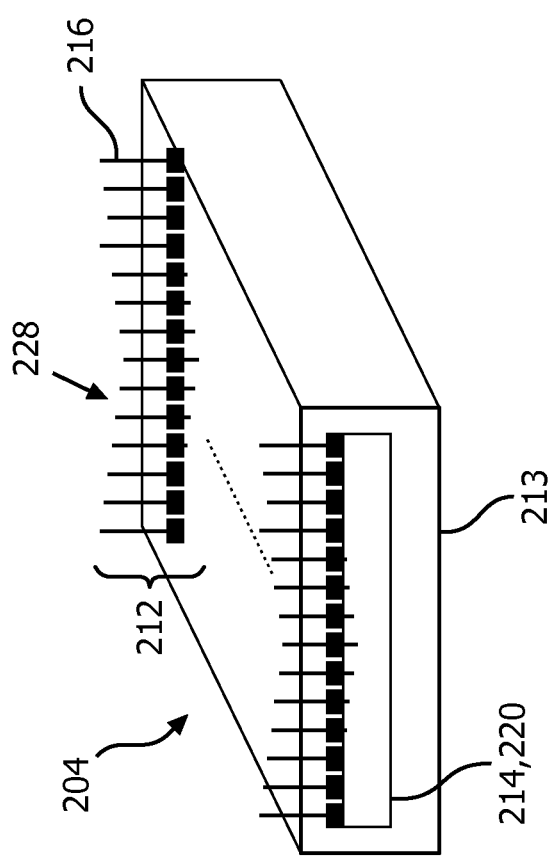
Figure 6:
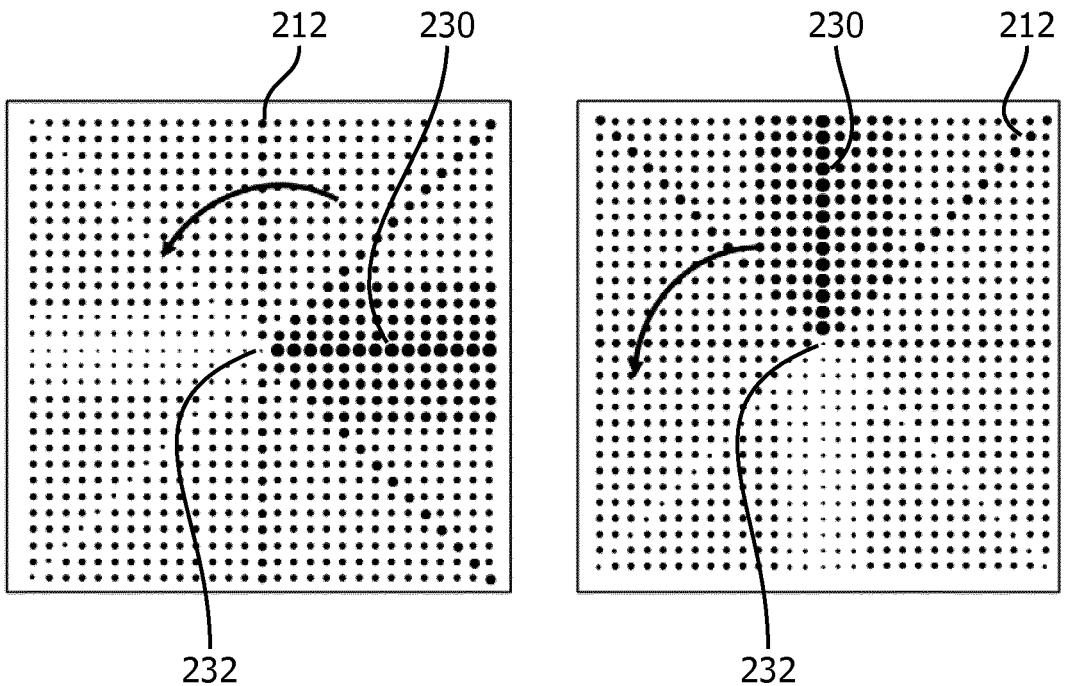
FIG. 6 is a schematic drawing of a mechanical wave generated using the nail board transducer according to the first embodiment in a top view.
Figure 7:
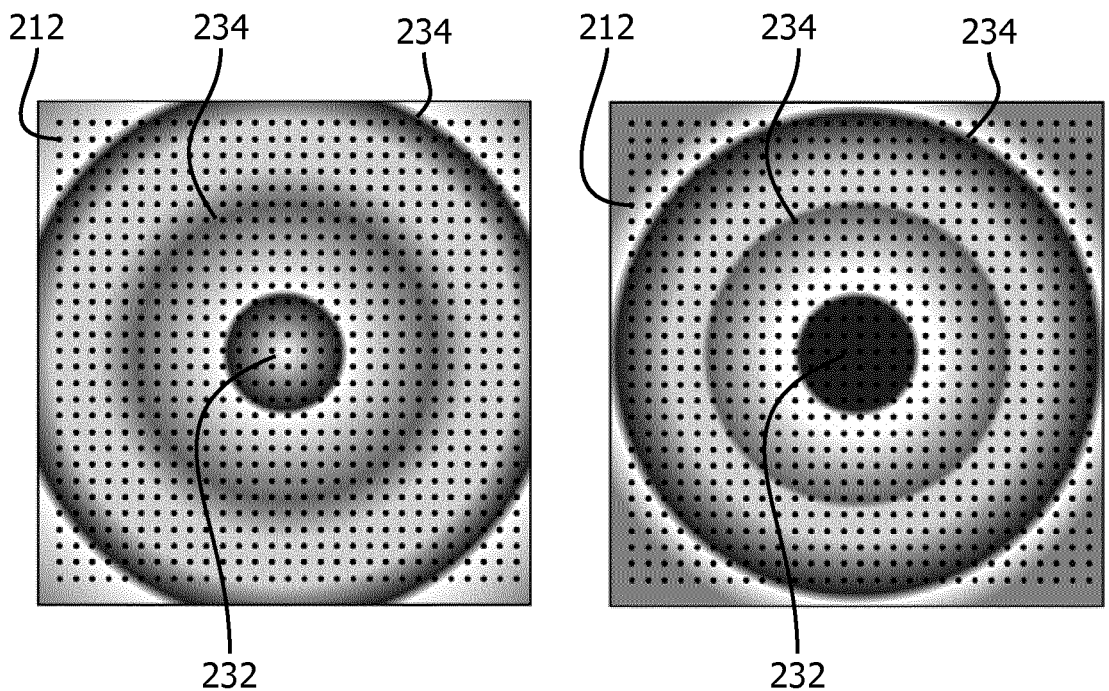
FIG. 7 is a schematic drawing of a mechanical wave generated using the nail board transducer according to the first embodiment in a top view.

The control unit 224 is configurable so that depending on the received drive signal from the driving device 206, different modes for generating mechanical waves can be chosen. Some modes can be seen in FIGS. 5, 6, and 7 by way of example. FIG. 5 shows a butterfly mode, where rows 228 of transducers 212 are driven simultaneously to provide a wave, which extends from a central row 228 of the rheology transducer device 204 towards the rows 228 at both sides. As can be seen in FIG. 6, another possible mode is a circular rotating mode. In the circular rotating mode, lines 230 of transducers 212, which rotate around a center 232 of the rheology transducer device 204, are simultaneously excited, i.e. the transducers 212 of the line 230 are equally excited. As can be seen in FIG. 7, a further possible mode is a radial mode. In the radial mode, the excitation of the transducers 212 is controlled, so that circles 234 of transducers 212 are equally excited. The excitation shifts from the center 232 of the rheology transducer device 204 outwards.

Figure 8:
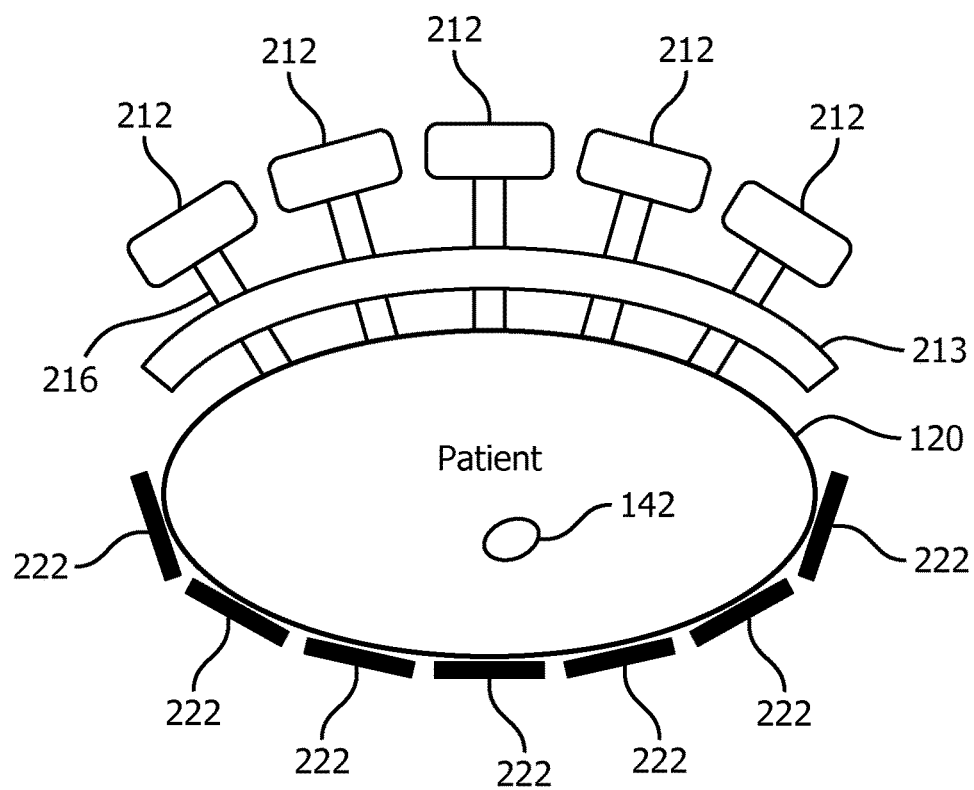
FIG. 8 is a schematic drawing showing a rheology transducer device and a sensor device of a rheology system of the MR rheology system of FIG. 2 according to a second embodiment.

The sensor device 208 of the first embodiment, which can be seen in FIG. 2, is shown in more detail in FIG. 8, which in general corresponds to the second embodiment. Nevertheless, the sensor device 208 of the first and second embodiments are identical, so that the details are also valid for the sensor device 208 of the first embodiment.

The sensor device 208 comprises multiple sensors 222 for sensing mechanical waves at the subject of interest 120. The sensors 222 are commonly arranged to sense mechanical waves at different locations of the subject of interest 120 with equal distances between each in a two-dimensional net-like structure. The structure is flexible to allow adaptation to different shapes depending on the area of the subject of interest 120 where the sensors 222 are located. The sensors 222 in this embodiment are acoustic sensors and are implemented as independent reception channels. The sensor device 208 is provided with a single cable for connection to the control device 210 to transmit signals of all sensors 222 thereto.

The MR imaging system 110 of the MR rheology system 200 is adapted to provide MR imaging information to the control device 210 of the rheology system 202, as can be seen in FIG. 2.

As can be seen in detail in FIG. 2, the control device 210 comprises a controller 240, which has implemented an optimization algorithm, as discussed later in detail. A control panel 242 is provided as user interface to an operator 244, who can set-up the rheology system 202. In an alternative embodiment, the control device 206 is provided integrally with the MR imaging system 110, so that the operator 244 can operate both systems 110, 202 together.

A MR rheology system 200 according to a second embodiment is mostly identical to the MR rheology system 200 according to the first embodiment. Differences exist in respect to the rheology transducer device 204 and the current sensors, as describe in detail below with respect to FIGS. 8 and 9. Hence, like components of the MR rheology system 200 of the second embodiment are denoted with the same reference numerals as those used in respect to the first embodiment. Details of the MR rheology system 200 of the second embodiment, which do not differ from those of the MR rheology system 200 of the first embodiment, are not described in detail. In particular, the operation of the MR rheology system 200 according to the first and second embodiments is in general identical.

Figure 9:
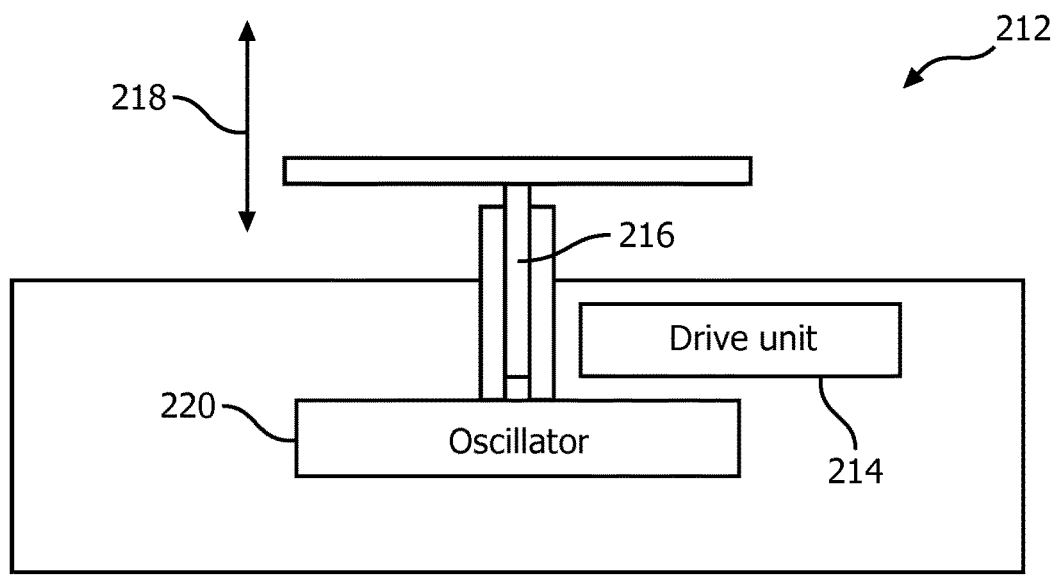
FIG. 9 is a schematic drawing of a single transducer of the rheology transducer device shown in FIG. 8.

A rheology transducer device 204 according to the second embodiment can be seen with respect to FIG. 8. The rheology transducer device 204 comprises multiple transducers 212 and is provided with a pre-shaped form for optimized coupling of the transducers 212 to the subject of interest 120. The transducers 212 are commonly attached to a fixture 213, which has a curved form to achieve the pre-shaped form of the rheology transducer device 204. Nevertheless, the fixture 213 of the second embodiment is still flexible to enable reliable adaption to the shape of the subject of interest 120. As can be seen in FIG. 9 in detail, each transducer 212 comprises a drive unit 214, which receives a drive signal from the driving device 206, a piston 216, which is movable in the direction of its longitudinal axis, as indicated by arrow 218, by an oscillator 220. Accordingly, each transducer 212 in contact with the subject of interest 120 can introduce a mechanical wave into the subject of interest 120 by movement of its piston 216. The transducers 212 are each individually connectable to a drive signal from the driving device 206, and all transducers 212 are directly driven from the driving device 206 via their drive unit 214.

The sensor device 208 of the second embodiment, which is shown in FIG. 8, has already been described identical before. As already stated, the sensor device 208 of the first and second embodiment is identical, so that no further description is given here.

The MR imaging system 110 of the MR rheology system 200 is adapted to provide MR imaging information to the control device 210 of the rheology system 202, as can be seen in FIG. 2. Furthermore, in a way not shown in the figures, the MR rheology system 200 is provided with current sensors for sensing the current driving the transducers 212. The current sensors provide sensor signals to the control device 210.

Figure 10:
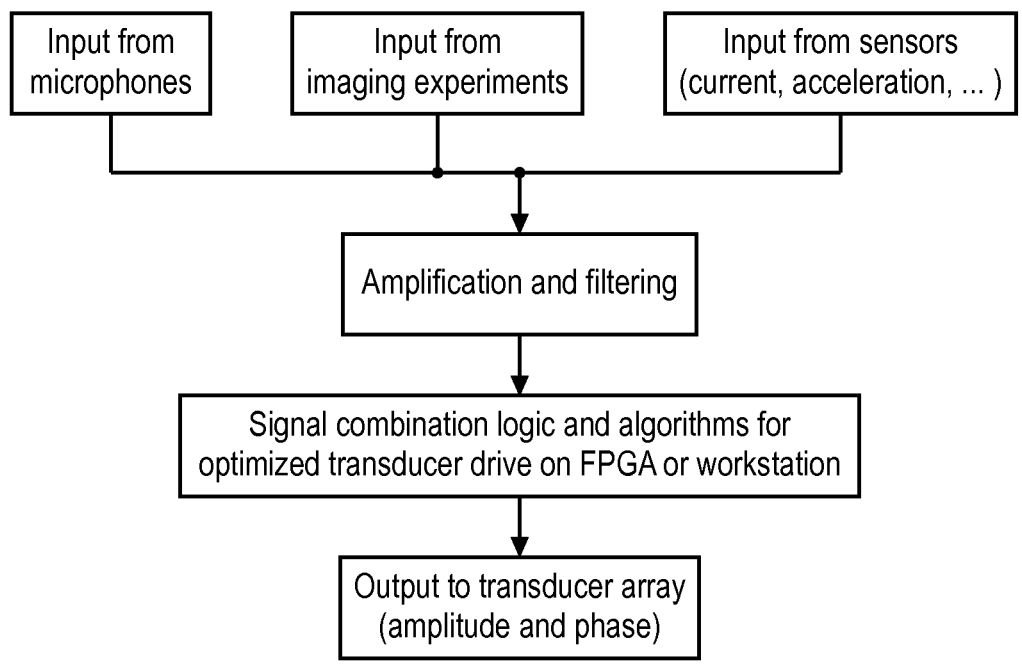
FIG. 10 is a diagram indicating the signal processing for feedback control using the MR rheology device of FIG. 8.

As can be seen in FIG. 10, the control device 210 of the second embodiment receives input from the sensors 222, the current sensors, and the MR imaging information from the MR imaging system 110. The received signals are amplified and filtered, and the control device 210 processes these signals for controlling the driving device 206. This processing is so far identical to that of the control device 210 of the first embodiment, except for the processed signals. According to the first embodiment, no current sensors are provided to provide signals to the control device, so that the control device 210 processes less signals for controlling the driving device 206.

Next will be described different methods for using the rheology system 202 and the MR rheology system 200 with reference to FIGS. 11 to 13.

Figure 11:
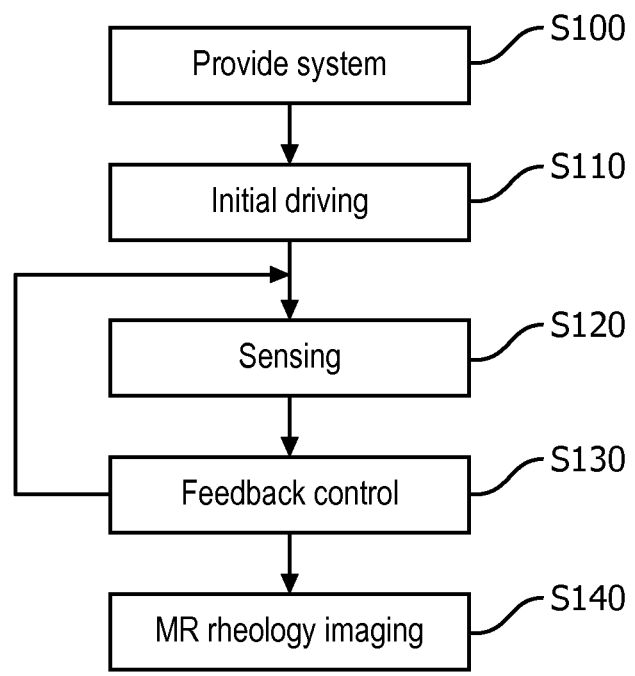
FIG. 11 is a flow chart indicating a first method for MR rheology imaging.

A first method, which is a MR rheology method, is shown in FIG. 11. In step S100, a MR rheology system 200 as described above in respect to the first or second embodiment is provided. The rheology transducer device 204 and the sensor device 208 are located at the subject of interest 120, whereby the rheology transducer device 204 and the sensor device 208 are brought into contact with the subject of interest 120. The sensor device 208 is located at an opposite side of the subject of interest 120 compared to the rheology transducer device 204. Furthermore, the subject of interest 120 is already located in the examination space 116 of the MR imaging system 110.

In step S110, the control device 210 drives the rheology transducer device 204 to introduce mechanical waves into the subject of interest 120 according to an initial setup of the operator 244. Hence, the transducers 212 provide spatially separated excitations of mechanical waves, each of which adjusted in amplitude and frequency as well as excitation phase relative to the other transducers 212.

In step S120, the mechanical waves at the subject of interest 120 are sensed using the sensor device 208.

In step S130, the control device 210 performs feedback control for driving the rheology transducer device 204 based on the mechanical waves sensed using the sensor device 208. Hence, mechanical waves inside the subject of interest 120, e.g. propagation direction, amplitude and phase distribution of the region of interest 142, are determined. This information is processed to control the driving device 206 to excite mechanical waves in the region of interest 142 as desired. Accordingly, the transducers 212 are driven in respect to frequency, amplitude, and phase to steer the mechanical wave into the region of interest 142 using interferences between individual mechanical excitations of the transducers 212, similar to e.g. 'beam steering' as known from HIFU devices. This includes based on the multichannel sensing of the mechanical wave with the sensor device 208 acoustic shimming of amplitude and phase of the introduced mechanical wave to excite deep lying tissue, i.e. tissue deep below a surface of the subject of interest 120, as well as directing a mechanical wave into a desired region of interest 142.

Steps S120 and S130 are continuously repeated, until the desired mechanical wave in the region of interest 142 is achieved. The step can further be repeated during subsequent step S140.

In step S140, the MR imaging system 110 performs MR image generation containing rheology information of the region of interest 142 of the subject of interest 120. The phase of the mechanical waves is adjusted relative to an acquisition signal indicating the beginning of an MR imaging sequence of the MR imaging system 110.

In an alternative embodiment of the method and the rheology system 202, the control device 210 of the rheology system 202 comprises a look-up table containing drive information based on typical anatomies and sizes of a subject of interest 120 for driving the multiple transducers 212. Accordingly, in steps S110 and S130 driving of the transducers 212 is adjusted using the lookup-tables. Hence, the information from the look-up table is preferably combined with input to the control device 210 e.g. from the sensor device 208, the MR imaging system 110 and/or the current sensors.

Figure 12:
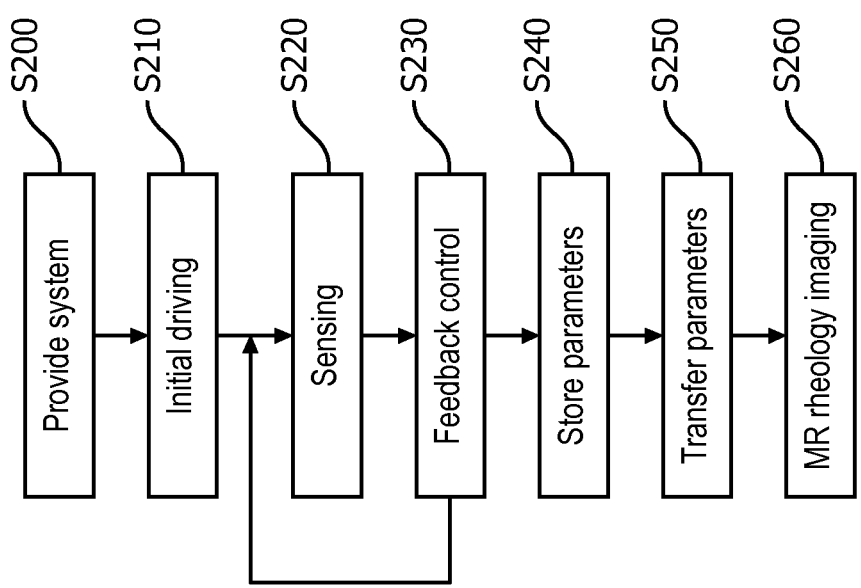
FIG. 12 is a flow chart indicating a second method for MR rheology imaging.

A second method, which is a MR rheology method, is shown in FIG. 12. The method includes a rheology method covering steps S200 to S240. In particular steps S200 to S230 correspond to prior steps. Details given in respect to steps 100 to 130 also apply to steps S200 to S230.

In step S200 a rheology system as specified above is provided. The rheology transducer device 204 and the sensor device 208 are located at the subject of interest 120, whereby the rheology transducer device 204 and the sensor device 208 are brought into contact with the subject of interest 120. The sensor device 208 is located at an opposite side of the subject of interest 120 compared to the rheology transducer device 204.

In step S210, the control device 210 drives the rheology transducer device 204 to introduce mechanical waves into the subject of interest 120 according to an initial setup of the operator 244.

In step S220, the mechanical waves at the subject of interest 120 are sensed using the sensor device 208.

In step S230, the control device 210 performs feedback control for driving the rheology transducer device 204 based on the mechanical waves sensed using the sensor device 208. Hence, mechanical waves inside the subject of interest 120, e.g. propagation direction, amplitude and phase distribution of the region of interest 142, are determined. This information is processed to control the driving 206 device to excite mechanical waves in the region of interest 142 as desired. Accordingly, the transducers 212 are driven in respect to frequency, amplitude, and phase to steer the mechanical wave into the region of interest 142 using interferences between individual mechanical excitations of the transducers 212, similar to e.g. 'beam steering' as known from HIFU devices.

Steps S220 and S230 are continuously repeated, until the desired mechanical wave in the region of interest 142 is achieved.

In step S240, the rheology system 202 stores control parameters according to the feedback control for driving the rheology transducer device 204. With the stored parameters, the MR imaging system 110 can be used for MR rheology imaging without real-time feedback control.

In step S250, the control parameters are transferred to the MR imaging system 110. Furthermore, also the subject of interest 120, who keeps connected to the rheology transducer device 204 with the driving device 206, is transferred into the examination space 116 of the MR imaging system 110. Accordingly, the positioning of the transducers 212 is maintained.

In step S260, the MR imaging system 110 performs MR image generation containing rheology information of the region of interest 142 of the subject of interest 120. The MR imaging system 110 is connected with the MR rheology device 204 to control the MR rheology device 204 based on the stored parameters. A control device of the MR imaging system, e.g. the MR imaging system control unit 126, performs the control of the MR rheology device 204 using the driving device 206.

Figure 13:
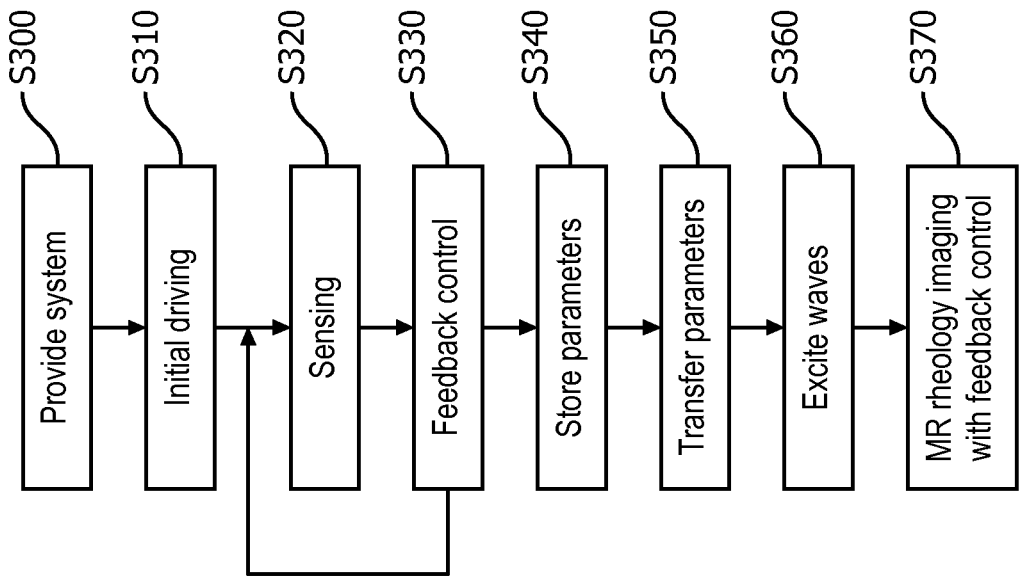
FIG. 13 is a flow chart indicating a third method for MR rheology imaging.

A third method, which is a MR rheology method, is shown in FIG. 13. The method is based on the rheology method described with respect to FIG. 12. Accordingly, steps S300 to S350 are performed as described above in respect to steps S200 to S250. The only difference is that the complete rheology system 202 stays with the subject of interest 120 during the entire method, e.g. through steps S300 to S350.

In subsequent step S360, mechanical waves are introduced into the region of interest 142 of the subject of interest 120 based on the stored control parameters.

In step S370 MR image generation containing rheology information of the region of interest 142 of the subject of interest 120 is performed. The phase of the mechanical waves is adjusted relative to an acquisition signal indicating the beginning of an MR imaging sequence of the MR imaging system 110. The MR rheology method provides MR rheology images of the region of interest. Step S370 comprises performing continuous feedback control of the rheology transducer device 204, as already described with respect to steps S320 and S330. The continuous feedback control refers to real-time adaptation of the mechanical wave inside the subject of interest 120.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 110 magnetic resonance (MR) imaging system
112 magnetic resonance (MR) scanner
114 main magnet
116 RF examination space
118 center axis
120 subject of interest
122 magnetic gradient coil system
124 RF screen
126 MR imaging system control unit
128 monitor unit
130 MR image reconstruction unit
132 control line
134 RF transmitter unit
136 RF switching unit
138 control line
140 radio frequency (RF) antenna device
142 region of interest
200 MR rheology system
202 rheology system
204 rheology transducer device
206 driving device
208 sensor device
210 control device
212 transducer
213 fixture
214 drive unit
216 piston
218 arrow
220 oscillator
222 sensor
224 control unit
226 internal sensor
228 row
230 line
232 center
234 circle
240 controller
242 control panel
244 operator

The invention claimed is:

1. A rheology system comprising:
a rheology transducer device for introducing mechanical waves into a subject of interest,
a driving device for driving the rheology transducer device,
a sensor device for sensing the mechanical waves that have traversed the subject of interest, the sensor device being disposed at an opposite side of the subject of interest from the rheology transducer device, and
a control device for receiving an input from the sensor device and for controlling the driving device based on the input received from the sensor device to excite the mechanical waves in a region of interest,
wherein
the rheology transducer device is provided as a nail board transducer device comprising a fixture and a plurality of longitudinally elongated transducers,
the plurality of longitudinally elongated transducers are commonly arranged and attached to the fixture to be commonly located at the subject of interest,
the nail board transducer device is configured to switch between an adjustment mode in which the plurality of longitudinally elongated transducers are movable in a longitudinal direction relative to the fixture to adapt to a shape of the subject of interest and an operational mode in which the plurality of longitudinally elongated transducers are not movable in the longitudinal direction relative to the fixture to adapt to the shape of the subject of interest,
the sensor device for sensing the mechanical waves that have traversed the subject of interest comprises multiple sensors configured to be placed in contact with the subject of interest for sensing the mechanical waves at different locations of the subject of interest; and the control device is configured to control an RF antenna and gradient coils of a magnetic resonance (MR) imaging system to implement an MR pulse sequence to cause MR signals to be emitted from the region of interest concurrent with (a) sensing the mechanical waves that have traversed the subject of interest with the multiple sensors and (b) adjusting the driving of the rheology transducer device to control a frequency, amplitude, and phase of the mechanical waves.

2. The rheology system according to claim 1, wherein the multiple sensors for sensing the mechanical waves that have traversed the subject of interest are commonly arranged with predefined distances between each other in a net structure configured to adapt to a shape of the subject.

3. The rheology system according to claim 1, wherein the rheology transducer device includes one or more oscillators configured to drive the plurality of longitudinally elongated transducers in the operational mode to introduce the mechanical waves into the region of interest of the subject of interest upon reception of a single driving signal from the driving device.

4. The rheology system according to claim 1, wherein the rheology transducer device includes one or more oscillators configured to drive the plurality of longitudinally elongated transducers in the operational mode to introduce the mechanical waves into the region of interest of the subject of interest according to a pre-defined pattern.

5. The rheology system according to claim 1, wherein the plurality of longitudinally elongated transducers are each individually connected to an oscillator configured to introduce the mechanical waves in response to a drive signal from the driving device.

6. The rheology system according to claim 1, comprising: a look-up table containing drive information based on typical anatomies and sizes of the subject of interest for driving the plurality of longitudinally elongated transducers.

7. The rheology system according to claim 1, in which wherein
the plurality of longitudinally elongated transducers are mounted in the fixture in a two-dimensional array equidistant from each other along at least one dimension of the fixture.

8. A magnetic resonance (MR) rheology system comprising:
the rheology system according to claim 1; and
the MR imaging system configured to control the rheology system.

9. A rheology method comprising:
providing the rheology system according to claim 1 with the rheology transducer device and the sensor device in contact with and adapted to the shape of the subject of interest,
with the driving device, driving the rheology transducer device to introduce the mechanical waves into the subject of interest,
sensing the mechanical waves that have traversed the subject of interest using the sensor device in contact with the subject of interest and generating a measured data signal indicative thereof, and
feeding back the measured data signal to the driving device to adjust driving the rheology transducer device based on the mechanical waves sensed using the sensor device.

10. A rheology method comprising:
providing the rheology system according to claim 1 with the rheology transducer device and the sensor device in contact with and adapted to the shape of the subject of interest,
storing control parameters for driving the rheology transducer device to introduce the mechanical waves into the subject of interest without feedback control, and
with the driving device, driving the rheology device using the stored control parameters.

11. The rheology method according to claim 10, further including:
introducing the mechanical waves into the region of interest of the subject of interest based on the stored control parameters, and
with an MR imaging system, performing MR image generation containing rheology information of the region of interest of the subject of interest concerning a stiffness of tissues of the subject of interest in an examination space of the MR imaging system.

12. A magnetic resonance (MR) rheology method comprising:
providing the MR rheology system according to claim 8 including the rheology transducer device and the sensor device in contact with the subject of interest,
driving the rheology transducer device to introduce the mechanical waves into the subject of interest,
placing the multiple sensors in contact with the subject of interest displaced from the rheology transducer device,
sensing the mechanical waves traversing the subject of interest using the multiple sensors,
adjusting the driving of the rheology transducer device based on the mechanical waves sensed using the multiple sensors,
generating MR image data of the region of interest of the subject of interest concurrently with the driving of the rheology transducer device, and
adjusting a phase of the mechanical waves relative to a beginning of an MR pulse sequence for the generating of the MR image data.

13. A software package for upgrading a magnetic resonance (MR) imaging system, wherein the software package contains instructions stored in a non-transitory computer readable medium for controlling the MR imaging system and the rheology transducer device for introducing the mechanical waves into the subject of interest, wherein the mechanical waves cause image data generated by the MR imaging system to be indicative of stiffness of soft tissue in the subject of interest according to the rheology method according to claim 11.

14. A software package for upgrading a magnetic resonance (MR) imaging system, wherein the software package contains instructions stored in a non-transitory computer readable medium for controlling the MR imaging system and a rheology system including a rheology transducer device for introducing mechanical waves into a subject of interest, a driving device for driving the rheology transducer device, a sensor device for sensing the mechanical waves that have traversed the subject of interest, the sensor device being disposed at an opposite side of the subject of interest from the rheology transducer device, and a control device for receiving an input from the sensor device and for controlling the driving device based on the input received from the sensor device to excite the mechanical waves in a region of interest, wherein the rheology transducer device is provided as a nail board transducer device comprising a fixture and a plurality of longitudinally elongated transducers, the plurality of longitudinally elongated transducers are commonly arranged and attached to the fixture to be commonly located at the subject of interest, the nail board transducer device is configured to switch between an adjustment mode in which the plurality of longitudinally elongated transducers are movable in a longitudinal direction relative to the fixture to adapt to a shape of the subject of interest and an operational mode in which the plurality of longitudinally elongated transducers are not movable in the longitudinal direction relative to the fixture to adapt to the shape of the subject of interest, the sensor device for sensing the mechanical waves that have traversed the subject of interest comprises multiple sensors configured to be placed in contact with the subject of interest for sensing mechanical waves at the subject of interest, wherein the multiple sensors are arranged to sense the mechanical waves at different locations of the subject of interest and generate feedback signals indicative thereof to control:

a radio frequency (RF) antenna and gradient coils of the MR imaging system to implement an MR pulse sequence to cause MR signals to be emitted from the region of interest concurrent with (a) receiving the feedback signals from the multiple sensors, and (b) adjusting the driving of the rheology transducer device to control a frequency, amplitude, and phase of the mechanical waves, and generating an MR image containing rheology information of the region of interest of the subject of interest concerning tissue elasticity of the subject of interest.

15. A rheology system comprising:

a plurality of elongated transducers mounted to a fixture in a regular two-dimensional array with the transducers equidistant from each other in at least one dimension, the fixture and the plurality of elongated transducers being configured to adapt the plurality of elongated transducers to a first surface area of a subject adjacent an internal region of interest;

a driving circuit configured to drive the plurality of elongated transducers to transmit mechanical waves into and through the internal region of interest;

an array of sensors configured to be placed in contact with a second surface area of the subject opposite to the internal region of interest from the first surface area, the array of sensors being configured to sense the mechanical waves which have traversed the internal region of interest and generate feedback signals indicative thereof;

one or more controllers configured to control:

a radio frequency (RF) antenna and gradient coils of a magnetic resonance (MR) imaging system to implement an MR pulse sequence to cause MR signals to be emitted from the region of interest concurrent with (a) receiving the feedback signals from the multiple sensors, and (b) adjusting the driving of the plurality of elongated transducers to control a frequency, amplitude, and phase of the mechanical waves.

16. A magnetic resonance (MR) rheology system comprising:

the rheology system according to claim 15; and the MR imaging system configured to control the rheology system and generate an MR image containing rheology information of the internal region of interest of the subject concerning tissue elasticity of the subject.

17. The rheology system according to claim 15, further including:

the MR imaging system; and wherein the one or more controllers are configured to:

control the driving circuit to drive the plurality of elongated transducers to introduce the mechanical waves into the subject, control the array of sensors to sense the mechanical waves traversing the internal region of interest using the array of sensors, adjust the driving of the plurality of elongated transducers based on the mechanical waves sensed using the array of sensors, control the MR imaging system to generate MR image data from the internal region of interest indicative of a stiffness of tissues of the subject concurrently with the driving of the plurality of elongated transducers, and adjust a phase of the mechanical waves relative to a beginning of the MR pulse sequence to generate the MR image data.

18. A magnetic resonance (MR) rheology system comprising:

a main magnet configured to generate a magnetic field through an examination space;

magnetic gradient coils configured to create magnetic field gradients in the magnetic field in the examination space;

one or more radiofrequency (RF) antennae configured to excite magnetic resonance in a region of interest of a patient disposed in the examination space and receive MR signals from the region of interest;

a plurality of elongated pistons mounted to a fixture in a two-dimensional array equidistant from each other in two dimensions, the fixture and the plurality of elongated pistons being configured to adapt the plurality of elongated pistons to a contour of a first surface area of the patient adjacent the region of interest;

drivers configured to drive the plurality of elongated pistons longitudinally to transmit mechanical waves into and through the region of interest;

an array of sensors configured to be placed in contact with a second surface area of the patient opposite to the internal region of interest from the first surface area at different locations on the second surface area, the sensors being configured to sense the mechanical waves which have traversed the internal region of interest and generate feedback signals indicative thereof;

one or more controllers configured to:

control the one or more RF antennae and the gradient coils to implement an MR pulse sequence to cause the MR signals to be emitted from the region of interest concurrent with both (a) sensing, generating, and receiving the feedback signals, and (b) controlling the drivers based on the feedback signals to control a frequency, amplitude, and phase of the mechanical waves, control the drivers to adjust a phase of the mechanical waves relative to a beginning of the MR pulse sequence, reconstruct the MR signals into images of the region of interest.

19. The MR rheology system according to claim 18, wherein the drivers include one or more oscillators configured to drive the plurality of elongated pistons in an operational mode to introduce the mechanical waves into the region of interest according to a pre-defined pattern.

20. The MR rheology system according to claim 18, wherein
the plurality of elongated pistons are each individually connected to an oscillator configured to drive the pistons longitudinally to introduce the mechanical waves.

* * * * *